(12) United States Patent
Allen et al.

(10) Patent No.: US 7,481,818 B2
(45) Date of Patent: Jan. 27, 2009

(54) LANCING DEVICE WITH A FLOATING PROBE FOR CONTROL OF PENETRATION DEPTH

(75) Inventors: John Allen, Mendota Heights, MN (US); Lorin P. Olson, Scotts Valley, CA (US); Alan Doop, Medina, MN (US)

(73) Assignee: Lifescan, Milpitas, CA (US)

( * ) Notice: Subject to any disclaimer, the term of this patent is extended or adjusted under 35 U.S.C. 154(b) by 486 days.

(21) Appl. No.: 10/690,083

(22) Filed: Oct. 20, 2003

(65) Prior Publication Data

US 2005/0085839 A1 Apr. 21, 2005

(51) Int. Cl.
*A61B 17/32* (2006.01)
*A61B 5/151* (2006.01)

(52) U.S. Cl. ............... 606/181; 606/167; 606/182; 600/583

(58) Field of Classification Search ......... 606/181–185, 606/167–172; 600/573, 576, 583, 584
See application file for complete search history.

(56) References Cited

U.S. PATENT DOCUMENTS

| | | | |
|---|---|---|---|
| 4,203,446 A | 5/1980 | Schlussel et al. | |
| 4,449,529 A | 5/1984 | Burns et al. | |
| 4,517,978 A * | 5/1985 | Levin et al. | 606/182 |
| 4,653,513 A * | 3/1987 | Dombrowski | 600/578 |
| 5,318,584 A | 6/1994 | Argauer et al. | |
| 5,730,753 A | 3/1998 | Morita | |
| 5,857,983 A * | 1/1999 | Douglas et al. | 600/583 |
| 5,997,561 A * | 12/1999 | Bocker et al. | 606/182 |
| 6,022,366 A * | 2/2000 | Schraga | 606/181 |
| 6,045,567 A | 4/2000 | Taylor et al. | |
| 6,071,250 A | 6/2000 | Douglas et al. | |
| 6,306,152 B1 | 10/2001 | Verdonk et al. | |
| 6,319,210 B1 * | 11/2001 | Douglas et al. | 600/583 |
| 2002/0022789 A1 | 2/2002 | Perez et al. | |
| 2002/0050655 A1 | 5/2002 | Travis et al. | |

(Continued)

FOREIGN PATENT DOCUMENTS

WO   WO 2004/060159 A1   7/2004

OTHER PUBLICATIONS

European Search Report, dated Jan. 17, 2005, for European Appln. No. EP 04256423.

*Primary Examiner*—Todd E Manahan
*Assistant Examiner*—Kathleen Sonnett

(57) ABSTRACT

A lancing device includes a lancing mechanism, a floating probe and a pressure tip. The lancing mechanism includes a lancet carriage, a lancet holder slidably connected to the lancet carriage, and a lancet attached to the lancet holder. The pressure tip of the lancing device is configured for engaging a target site and creating a target site bulge. The floating probe is adapted to floatably contact the target site bulge and to operatively interact with the lance carriage to control a penetration depth of the lancet into the target site bulge. A method for lancing a target site includes providing the lancing device describe above and contacting the pressure tip of the lancing device with the target site. The pressure tip is then urged towards the target site to create a target site bulge with the floating probe of the lancing device floating on a surface of the target site bulge. Next, the target site bulge is lanced while the floating probe operatively interacts with the lance carriage to control a penetration depth of the lancet.

9 Claims, 8 Drawing Sheets

U.S. PATENT DOCUMENTS

| | | |
|---|---|---|
| 2002/0082522 A1 | 6/2002 | Douglas et al. |
| 2002/0177787 A1 | 11/2002 | Radwanski et al. |
| 2003/0050627 A1 | 3/2003 | Taylor et al. |
| 2004/0127818 A1* | 7/2004 | Roe et al. ............ 600/583 |
| 2004/0215224 A1* | 10/2004 | Sakata et al. .......... 606/181 |
| 2004/0236251 A1 | 11/2004 | Roe et al. |

* cited by examiner

LANCING DEVICE WITH A FLOATING PROBE FOR CONTROL OF PENETRATION DEPTH

BACKGROUND OF THE INVENTION

1. Field of the Invention

The present invention relates, in general, to lancing devices and, in particular, to lancing devices with penetration depth control and associated methods of use.

2. Description of the Related Art

Conventional lancing devices generally have a rigid housing and a lancet that can be armed and launched so as to briefly protrude from one end of the lancing device. For example, conventional lancing devices can include a lancet that is mounted within a rigid housing such that the lancet is movable relative to the rigid housing along a longitudinal axis thereof. Typically, the lancet is spring loaded and launched, upon release of the spring, to penetrate (i.e., "lance") a target site (e.g., a dermal tissue target site). A biological fluid sample (e.g., a whole blood sample) can then be expressed from the penetrated target site for collection and analysis. Conventional lancing devices are described in U.S. Pat. No. 5,730,753 to Morita, U.S. Pat. No. 6,045,567 to Taylor et al. and U.S. Pat. No. 6,071,250 to Douglas et al., each of which is incorporated fully herein by reference.

Lancing devices often include a cap that engages the target site. Such a cap has an aperture (i.e., opening), through which the lancet protrudes during use. Typically, a distal end of the cap will be placed in contact with the target site during use. The profile of the distal end of the cap can be adapted for contact with predetermined target sites, such as fingers, earlobes, forearms and the abdomen.

When a cap is contacted with a target site, pressure is usually applied to the target site prior to launch of the lancet. This pressure urges the cap against the target site and creates a target site bulge within the opening of the cap. The lancet is then launched to penetrate the target site bulge.

When pressure is applied on a cap of a lancing device against a target site, however, the height of the resultant target site bulge can vary greatly depending on the dimensions of the cap's opening, the magnitude of applied pressure and various physical properties (e.g., elasticity) of the target site. Such variability in target site bulge height causes the penetration depth of the lancet into the target site bulge to vary, as well. Thus, a lancet can potentially penetrate too deeply in some circumstances and not deeply enough, or at all, in other circumstances. Still needed in the field, therefore, is a lancing device and associated method that provide for the control of penetration depth across target site bulges of various heights.

SUMMARY OF THE INVENTION

Lancing devices and associated methods according to embodiments of the present invention provide for the control of penetration depth across target site bulges of various heights.

A lancing device according to an exemplary embodiment of the present invention includes a lancing mechanism, a pressure tip and a floating probe. The lancing mechanism includes a lancet carriage, a lancet holder slidably connected to the lancet carriage, and a lancet attached to the lancet holder. The pressure tip is configured for engaging a target site and creating a target site bulge. The floating probe is adapted to floatably contact the target site bulge and to operatively interact with the lance carriage to control a penetration depth of the lancet into the target site bulge.

Since the floating probe of lancing devices according to the present invention is adapted to float upon the target site bulge, the floating probe can provide mechanical feedback to the lance carriage, lancet holder and lancet such that the penetration depth across target site bulges of various heights is essentially constant. In doing so, the floating probe fixes a position of the lancet carriage relative to the target site bulge, thus providing a constant penetration depth.

A method for lancing a target site according to an exemplary embodiment of the present invention includes providing a lancing device (according to the present invention as described herein) and contacting a pressure tip of the lancing device with the target site. The pressure tip is then urged towards the target site to create a target site bulge with a floating probe of the lancing device floating on a surface of the target site bulge. Next, the target site bulge is lanced while the floating probe operatively interacts with the lance carriage to control a penetration depth of the lancet.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings, of which.

DETAILED DESCRIPTION OF THE INVENTION

Figure 1:
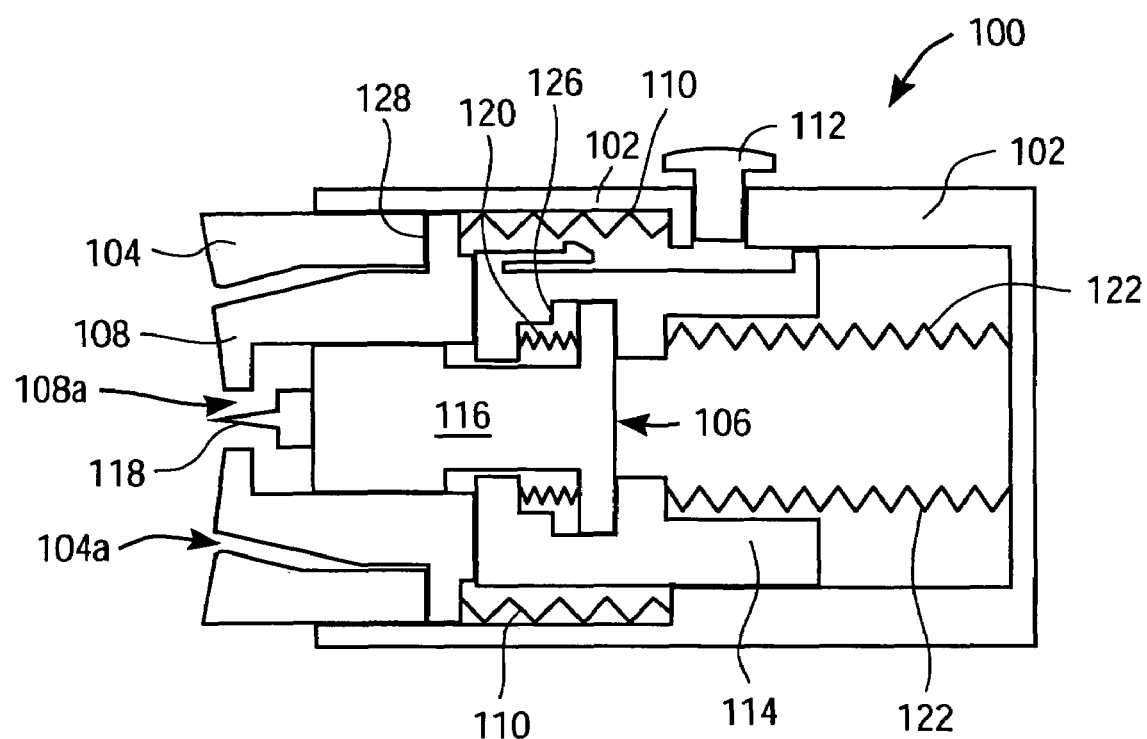
FIG. 1 is a simplified, schematic, cross-sectional view of a lancing device according to an exemplary embodiment of the present invention, with a floating probe and a lancing mechanism of the lancing device in a rest position.

FIG. 1 is a simplified, schematic cross-sectional view of a lancing device 100 according to an exemplary embodiment of the present invention. Lancing device 100 includes a housing 102, a pressure tip 104, a lancing mechanism 106, floating probe 108, a floating probe spring 110 and a trigger button 112. In the embodiment of FIG. 1, pressure tip 104 is attached to housing 102.

Pressure tip 104 and floating probe 108 are generally, but are not limited to being, cylindrical in form with openings (104a and 108a, respectively) therethrough. The openings within pressure tip 104 and floating probe 108 may be, but are not limited to, circular shape openings, square shape openings, triangular shape openings, C-shape openings, U-shape openings, hexagonal shape openings and an octagonal shape openings.

During use of lancing device 100, pressure tip 104 is pressed against a target site (e.g., a user's skin of a dermal tissue target site) such that pressure tip 104 engages (contacts) the target site and urges the target site into a target-site bulge (not shown in FIG. 1) within the opening of pressure tip 104.

Lancing mechanism 106 includes a lancet carriage 114, a lancet holder 116 and a lancet 118. Lancing mechanism 106 also includes over-travel spring 120 and launcher spring 122. Lancet carriage 114 includes carriage latch 124 and a lancet holder over-travel stop feature 126. In addition, pressure tip 104 has a probe stop surface 128.

Floating probe 108 of lancing device 100 is adapted to floatably contact a target site bulge (not shown in FIG. 1) and is configured to operatively interact with lance carriage 114 to control a penetration depth of lancet 118 into the target-site bulge. However, the extent to which floating probe 108 can move is limited by floating probe spring 110 and probe stop surface 128.

In the embodiment of FIG. 1, the floating nature of floating probe 108 is due to floating probe 108 being slidable along a longitudinal axis of housing 102. In addition, lancet carriage 114 and lancet holder 116 are also slidable with respect to housing 102 along the same longitudinal axis. Furthermore, lancet holder 116 is slidably connected to lancet carriage 114.

Over-travel spring 120, launcher spring 122 and probe spring 110 are configured to control movement and positioning of the floating probe, lancet carriage and lancet holder in a manner described below.

Over-travel spring 120 and lancet holder over-travel stop feature 126 provide for lancet 118 to extend to a controlled penetration depth in a target site bulge before over-travel spring 120 returns lancet 118 to a fixed rest position. In this regard, it should be noted that the position of lancet holder over-travel stop feature 126 with respect to a target site bulge is operatively set by the interaction of floating probe 108 and lancet carriage 114 (as described further below). Therefore, floating probe 108 is able to provide mechanical feedback to the lancet carriage 114, lancet holder 116 and lancet 118 such that the penetration depth across target site bulges of various heights is controlled and essentially constant.

Launcher spring 122 controls movement of the lancet carriage 114. Floating probe spring 110 and the probe stop surface 128 serve to control the extent to which the floating probe 108 can move (i.e., float) relative to housing 102. Exemplary, but non-limiting, strengths of the launcher spring 122, over-travel spring 120 and floating probe spring 110 are in the range of 0.5-1.0 lbs of force, 0.2-0.3 lbs of force and approximately 0.2 lbs of force respectively.

Pressure tip 104 can be formed of, for example, a rigid or a relatively resiliently deformable material, including, but not limited to, elastomeric materials, polymeric materials, polyurethane materials, latex materials, silicone materials and any combinations thereof. Floating probe 108 can be formed of any suitable material including, but not limited to, relatively rigid material such as acrylonitrile butadiene styrene plastic, injection moldable plastic, polystyrene and metallic materials.

Figure 2:
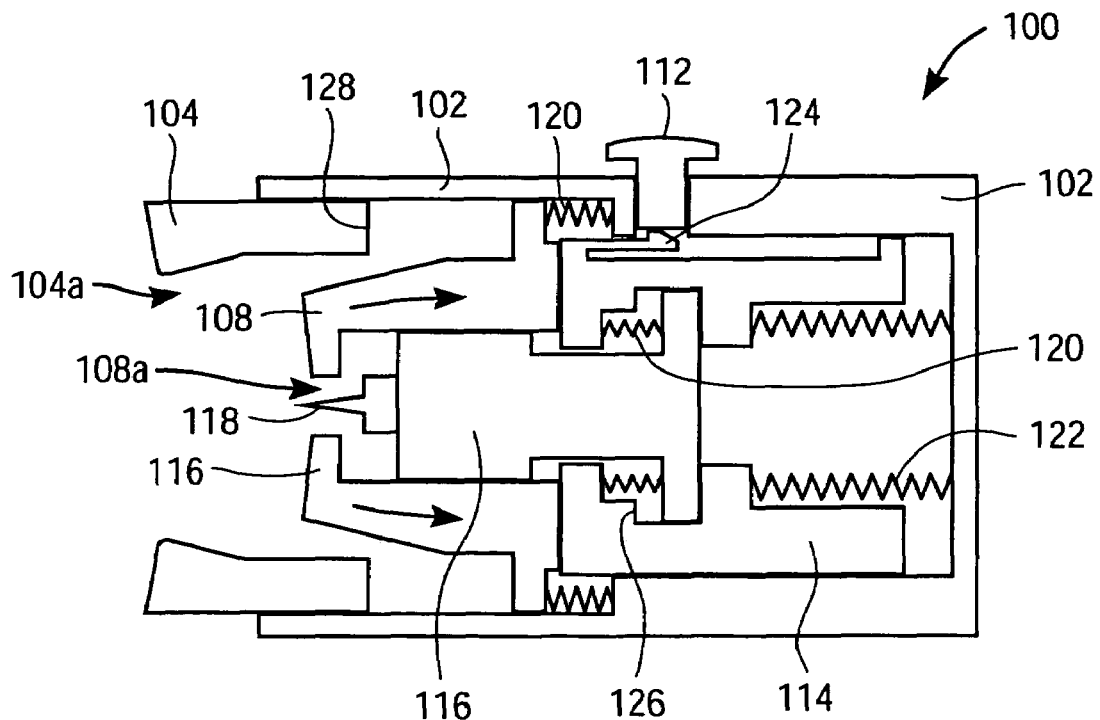
FIG. 2 is a simplified schematic, cross-sectional view of the lancing device of FIG. 1 with the floating probe and lancing mechanism in the act of being placed into an armed position.

The operation and various features of lancing device 100 are illustrated in FIGS. 2, 3A, 3B, 4A, 4B, 5A and 5B. FIG. 2 is a simplified schematic, cross-sectional view of lancing device 100 with the floating probe 108 and lancing mechanism 106 in the act of being placed into an armed position (e.g., immediately prior to use). In an armed position, the lancet carriage 114 is held in position against the biasing force of launcher spring 122 by interaction between carriage latch 124, housing 102 and trigger button 112. The arrows of FIG. 2 depict a direction in which floating probe 108 can be pushed in order to place lancet carriage 114 into a position where it is held against the biasing force of launcher spring 122 by interaction between carriage latch 124, housing 102 and trigger button 112 (i.e., into an armed position). Lancing device 100 can, however, be placed into an armed position by any methods known to one skilled in the art including, for example, use of an external slider (not shown) or a plunger (also not shown).

Figure 3A:
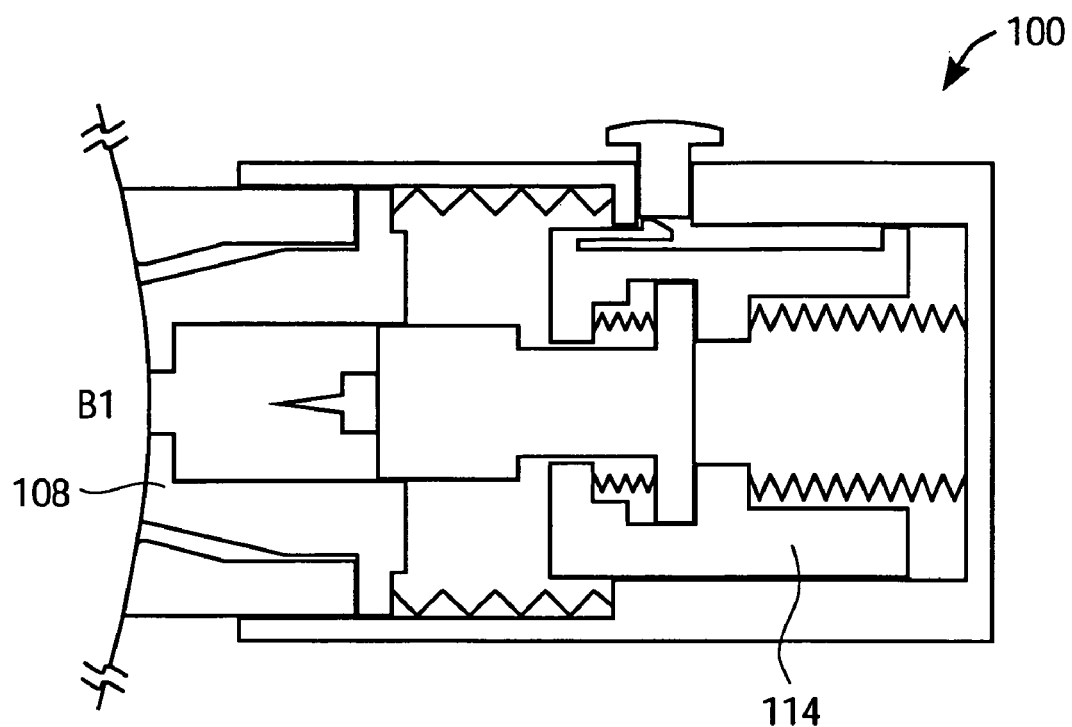
FIGS. 3A and 3B are simplified schematic, cross-sectional views of the lancing device of FIG. 1 with the floating probe contacting a relatively-low target site bulge and a relatively-high target site bulge, respectively.
Figure 3B:
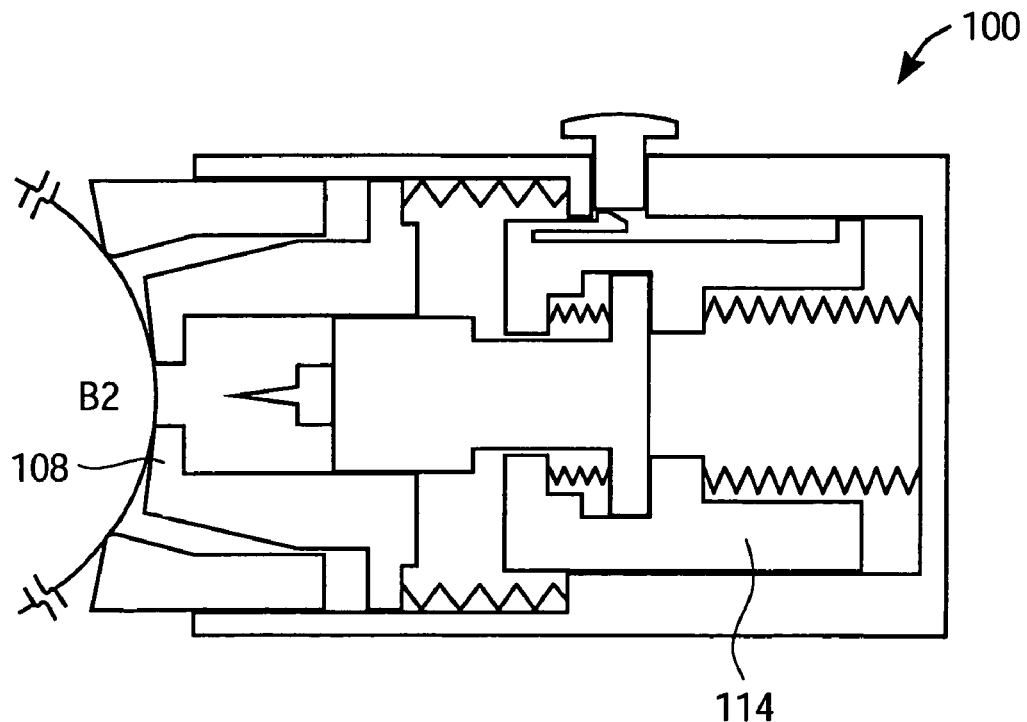

FIGS. 3A and 3B are simplified schematic, cross-sectional views of the lancing device of FIG. 1 with the floating probe contacting a relatively-low target site bulge (denoted as B1) and a relatively-high target site bulge (denoted as B2), respectively. When lancing device 100 is in use and pressure tip 104 is applied against a target site, a target site bulge is created in the opening of pressure tip 104. The height of the target site bulge can vary depending on, for example, target site physical properties. However, in both FIG. 3A and FIG. 3B, floating probe 108 rests upon the target site bulge (B1 and B2, respectively in the FIGS. 3A and 3B) and is configured to move (i.e., float) with the surface of the target site bulge, essentially independent of lancet carriage 114 and housing 102. Since the floating probe floats with the surface of the target site bulge, floating probe 108 serves to control the penetration depth of lancet 118 into the target site bulge (as explained in more detail below). One skilled in the art will recognize that floating probe 108 can be configured to essentially float (rest) on the surface of the target site bulge in the presence of floating probe spring 110. This can be accomplished by, for example, selecting a floating probe spring with a spring constant that does not significantly interfere with the floating nature of the floating probe.

Figure 4A:
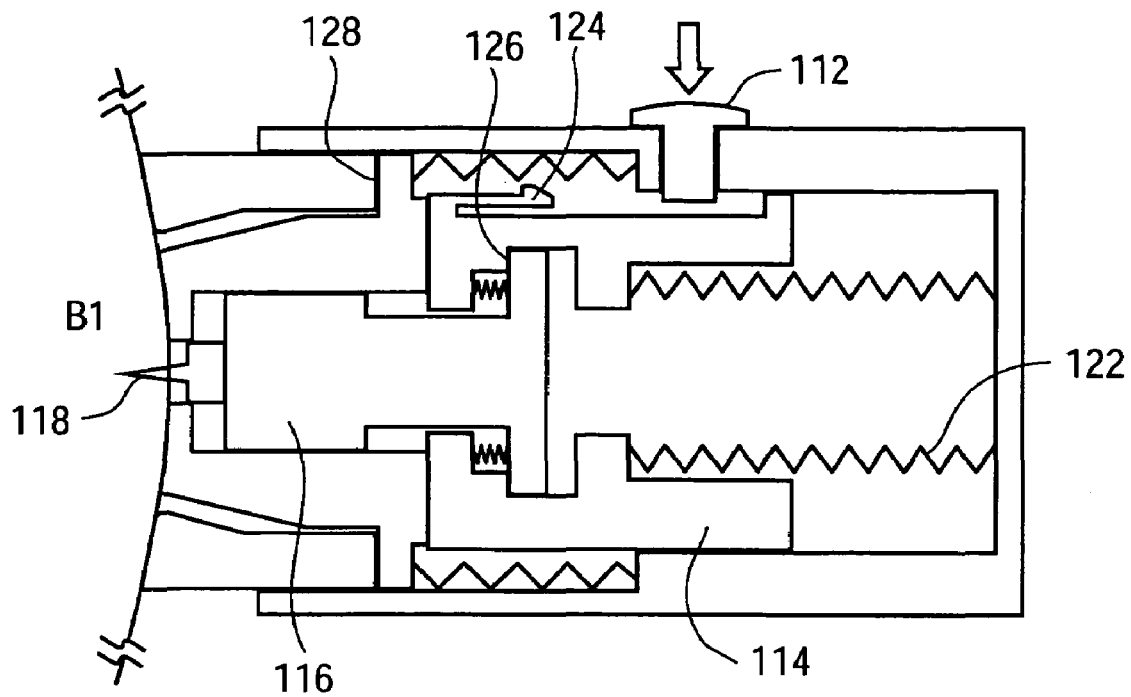
FIGS. 4A and 4B are simplified, schematic, cross-sectional views of the lancing device of FIG. 1 depicting lance penetration into a relatively-low target site bulge and a relatively-high target site bulge, respectively.
Figure 4B:
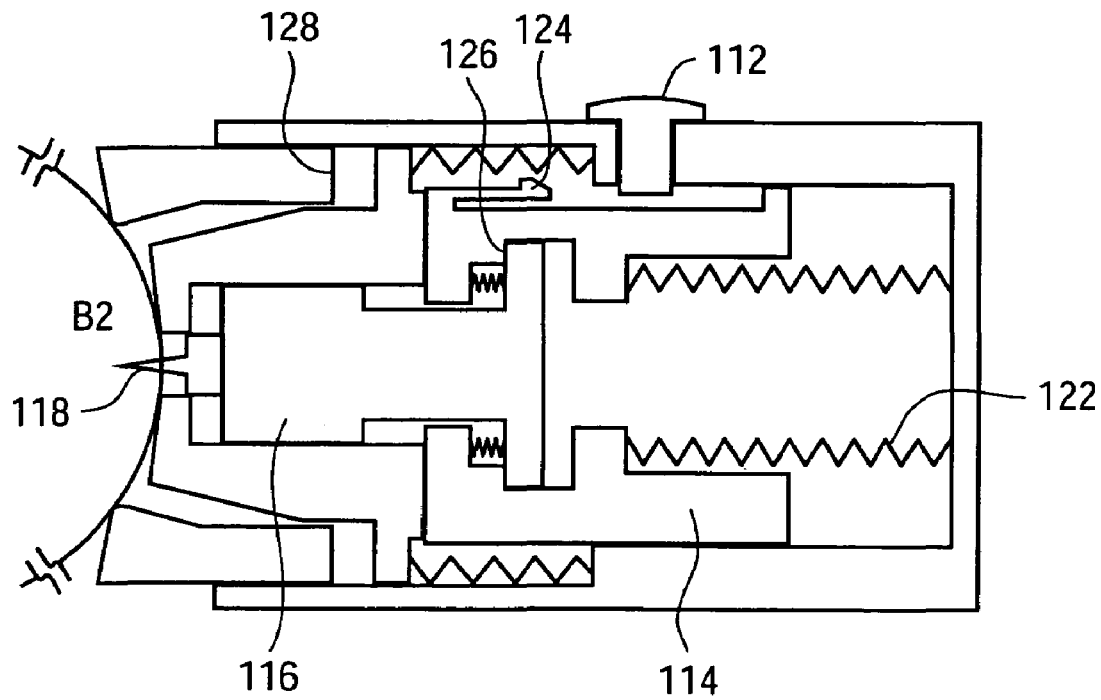

FIGS. 4A and 4B are simplified, schematic, cross-sectional views of lancing device 100 depicting lance penetration into the relatively-low target site bulge B1 and the relatively-high target site bulges B2 of FIGS. 3A and 3B, respectively. Once pressure tip 104 has been applied to a target site and a target site bulge created, operation of trigger button 112 (depicted by the arrow in FIG. 4A) releases carriage latch 124.

Release of carriage latch 124 allows lancet carriage 114, lancet holder 116 and lancet 118 to move (i.e., to be launched) toward the target site bulge under the force of launcher spring 122. Subsequently, lancet carriage 114 is stopped by contact with floating probe 108. The inertia of the lancet carriage may push the floating probe against the target site bulge, however this effect is a momentary deflection that is not expected to adversely affect operation of the lancing device.

Due to the inertia of lancet holder 116, lancet holder 116 and lancet 118 continue moving toward the target site bulge resulting in lancet 118 penetrating the target site bulge. This penetration is depicted in FIGS. 4A and 4B. Lancet holder over-travel stop feature 126 limits the distance that lancet holder 116 and lancet 118 can travel (to, for example, a distance in the range of 0.25 to 1.5 mm) once lancet carriage 114 has been stopped by contact with floating probe 108. The distance that lancet holder 116 and lancet 118 travel once lancet carriage 114 has been stopped is referred to as the over-travel distance. In the embodiment of FIGS. 1-5B, the over-travel distance is a fixed distance.

Since the floating probe rests upon the surface of the target site bulge, regardless of whether the target site bulge is relatively high or relatively low, and serves to stop the movement of lancet carriage 114, penetration depth is consistently controlled across various target site bulge heights.

Figure 5A:
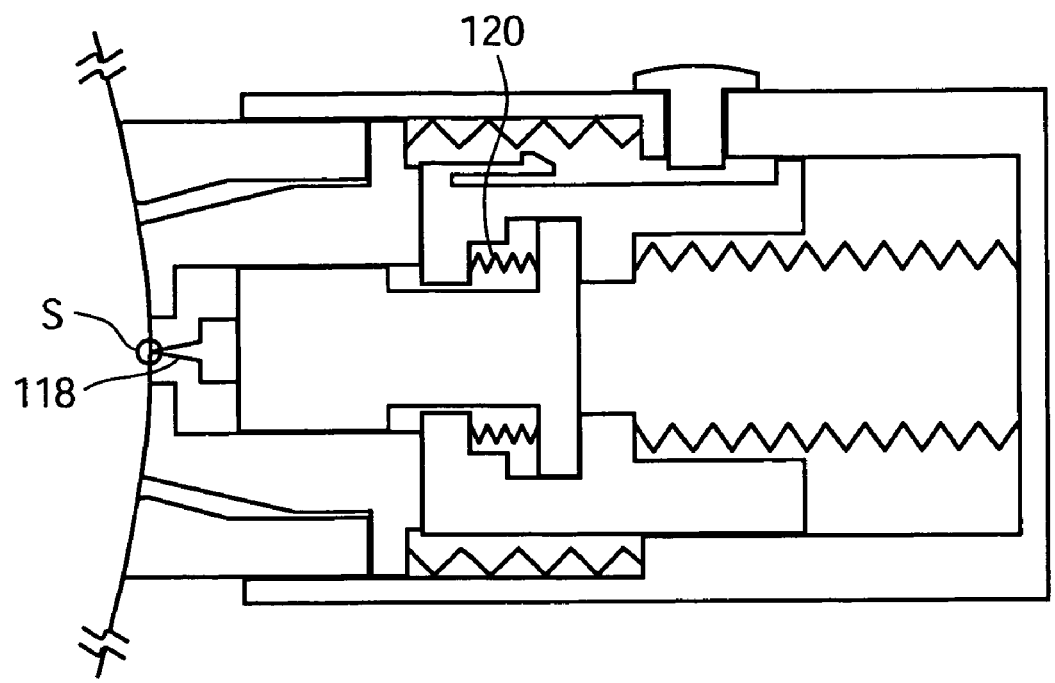
FIGS. 5A and 5B are simplified, schematic, cross-sectional views of the lancing device of FIG. 1 depicting post-lancing sample collection from a relatively-low target site bulge and a relatively-high target site bulge, respectively.
Figure 5B:
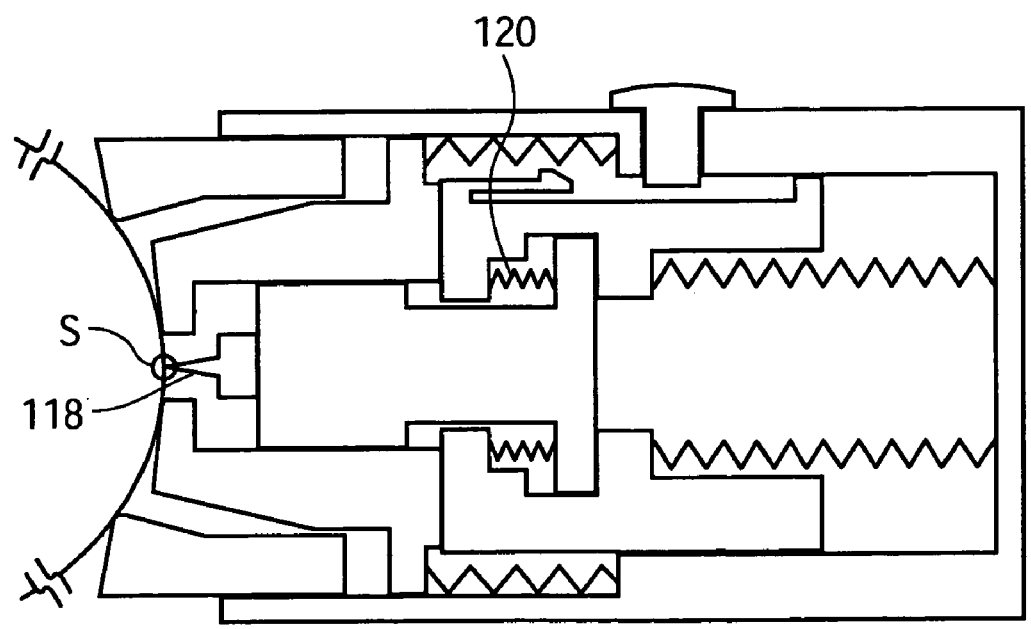

FIGS. 5A and 5B are simplified, schematic, cross-sectional views of a lancing device 100 depicting post-lancing sample collection from the relatively-low target site bulge B1 and a relatively-high target site bulge B2 of FIGS. 4A and 4B, respectively. Following penetration of the target site bulge by lancet 118 (as depicted in FIGS. 4A and 4B), the biasing force of over-travel spring 120 moves lancet holder 116 and lancet 118 to a position wherein lancet 118 is near or just below the surface of the target site bulge, e.g. to a depth of approximately 0.05 to 0.25 mm below the surface of the target site bulge. FIGS. 5A and 5B depict the presence of a biological fluid sample S (e.g., whole blood) that has been expressed from the target site bulge. This biological fluid sample is available for transfer to a test strip (not shown) for analyte detection.

Figure 6:
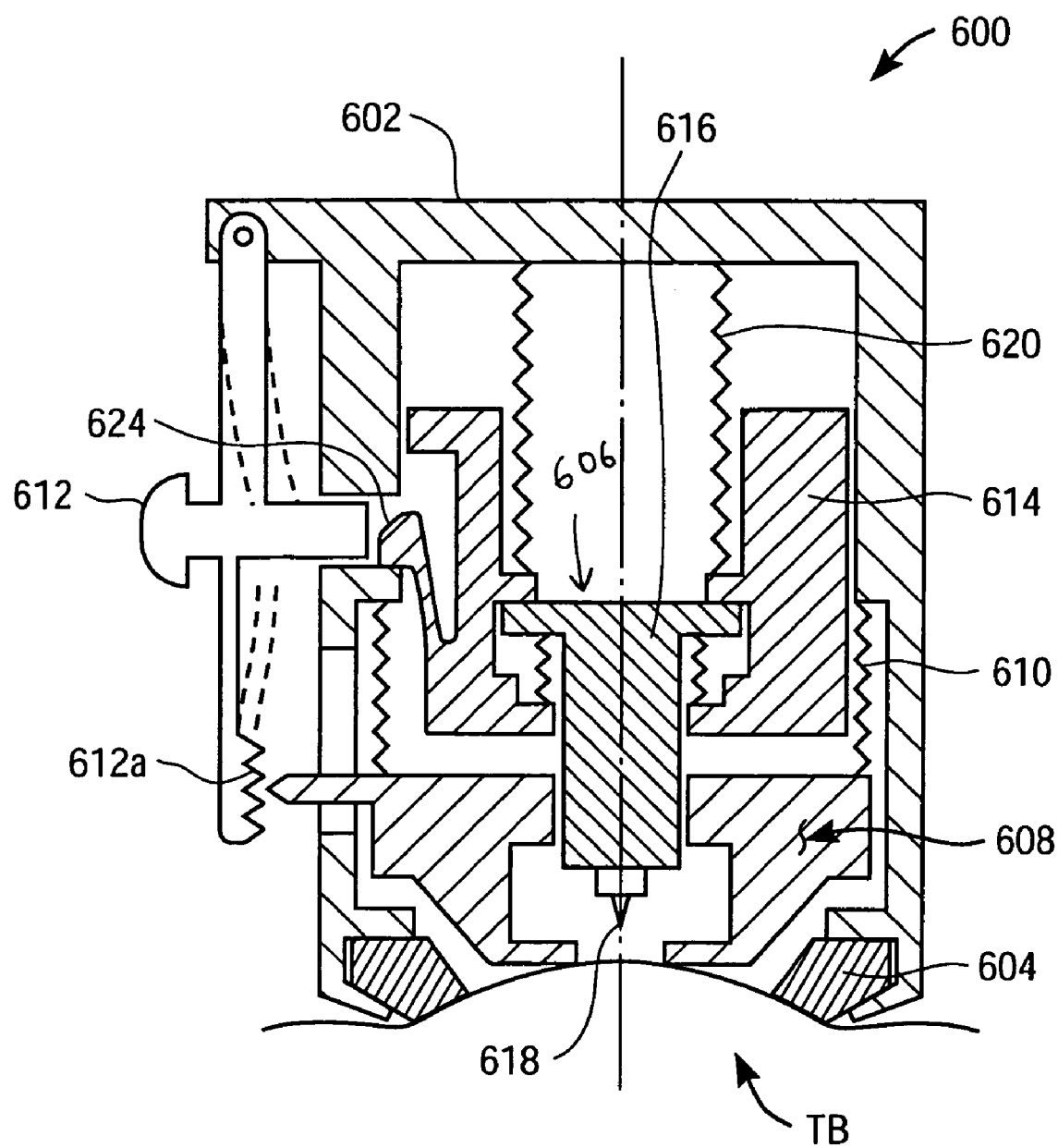
FIG. 6 is a simplified, schematic, cross-sectional view of a lancing device according to another exemplary embodiment of the present invention.

FIG. 6 is a simplified, schematic, cross sectional view of a lancing device 600 according to another exemplary embodiment of the present invention. In FIG. 6, lancing device 600 is depicted in an armed position and as pressed against a target site bulge (TB). Lancing device 600 includes a housing 602, a pressure tip 604, a lancing mechanism 606, floating probe 608, floating probe spring 610 and a stop lock assembly 612 (with the dashed lines indicating a flexed position of stop lock assembly 612).

Lancing mechanism 606 includes a lancet carriage 614, a lancet holder 616 and a lancet 618. Lancing mechanism 606 also includes launcher spring 620 and lancet carriage 614 includes a carriage latch 624.

Pressure tip 604 of lancing device 600 is depicted as an elastomeric cap, such as the cap described in U.S. Provisional Patent Application No. 60/426,683, which is hereby fully incorporated herein by reference. However, any suitable pressure tip known to those of skill in the art can be employed in embodiments of lancing devices according to the present invention.

Stop lock assembly 612 can be employed to prevent the floating probe 608 from moving after launching of the lancet carriage 614, thereby reducing the impact force between the lancet carriage and the floating probe. This is accomplished by pushing stop lock assembly 612 (in the direction of the arrow in FIG. 6) such that stop lock assembly teeth 612A engage floating probe 608. Once stop lock assembly teeth 612A have engaged floating probe 608, floating probe 608 is prevented from moving. Further pushing of stop lock assembly 612 places stop lock assembly into a flexed position (indicated by the dashed lines in FIG. 6) such that it can operatively interact with carriage latch 624.

Figure 7:
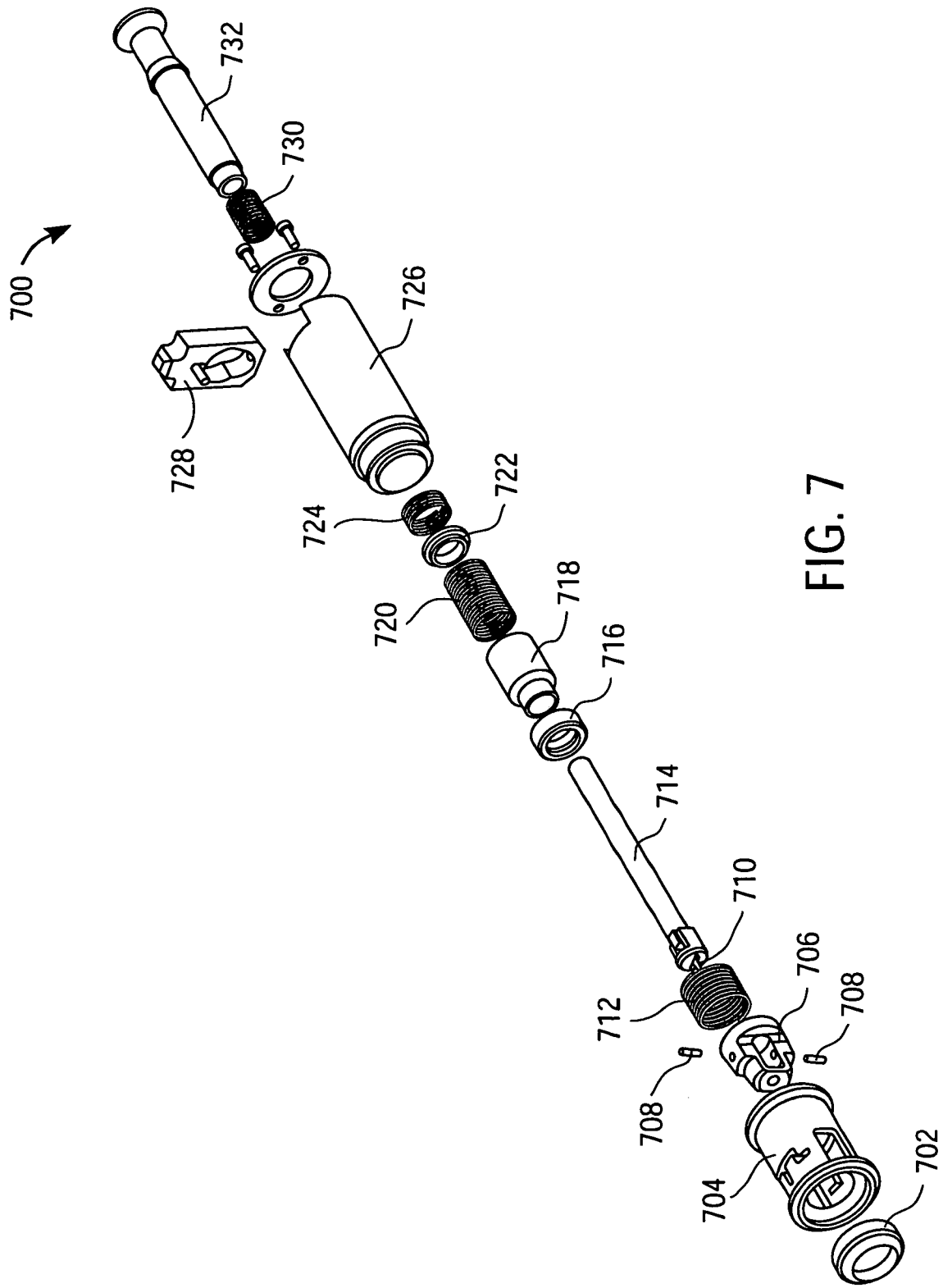
FIG. 7 is an exploded perspective view of a lancing device according to yet another exemplary embodiment of the present invention.
Figure 8:
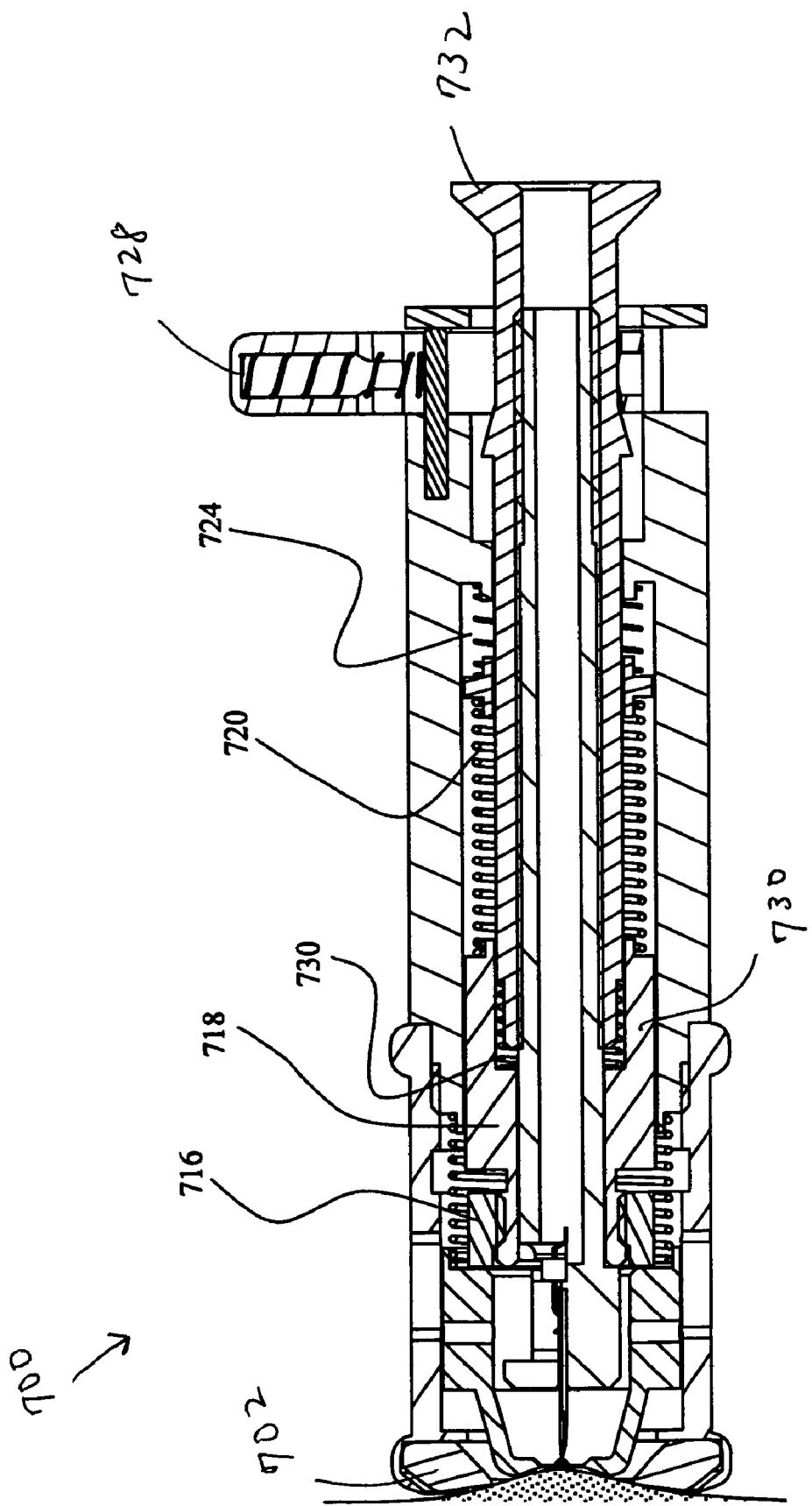
FIG. 8 is a simplified, schematic, cross-sectional view of the lancing device of FIG. 7.

FIGS. 7 and 8 are perspective exploded and cross-sectional views, respectively, of a lancing device 700 according to another exemplary embodiment of the present invention. Lancing device 700 includes a pressure tip 702, front housing 704, floating probe 706, dowel pins 708, lancet 710, floating probe spring 712, lancet holder 714, rest adjust nut 716, lancet carriage 718, launcher spring 720, decoupling spring spacer 722, decoupling spring 724, rear housing 726, trigger button 728, over-travel spring 730 and plunger 732.

Pressure tip 702 is illustrated as having the form of an elastomeric cap, such as the elastomeric cap described in U.S. Provisional Patent Application No. 60/426,683, which is fully incorporated herein by reference. In the embodiment of FIGS. 7 and 8, decoupling spring 724 is operatively "in line" with the launcher spring 720. Therefore, decoupling spring 724 is functionally in series with the launcher spring 720.

Decoupling spring 724 is selected to have a much lower spring load than the launcher spring 720. For example, decoupling spring 724 can have a spring load at equilibrium in the range of 0.1 to 0.2 lbs. Decoupling spring 724 serves to reduce the cumulative force on floating probe 706. In the absence of decoupling spring 724, the spring force on floating probe 706 would be a result of the combined forces of floating probe spring 712 and the launcher spring 720. This combined force would cause an increase in the effective spring rate at the floating probe 706 that could adversely affect the operational characteristics of pressure tip 702. However, decoupling spring reduces the combined force and, therefore, eliminates such adverse affects. For example, when launcher spring 720 is extended during use, decoupling spring 724 acts to reduce the force applied by launcher spring 720 against lancet carriage 718.

Lancing device 700 is configured such that it can be placed into an armed position by retraction of plunger pull 732. Trigger button 728 can, thereafter, be employed to initiate launching of lancet carriage 718 and lancet holder 714.

Rest adjust nut 716 is adapted to adjust the lancet rest position, while dowel pins 708 are configured for locking floating probe 706 into a fixed position. Rest adjust nut 716 allows the user to adjust the post-launching rest position of the lancet 710 relative to the floating probe 706. This adjustment enables placement of the lancet tip in a position that facilitates the transfer of a sample onto a test strip (not shown) integrated with the lancet. Optimal placement of a lancet after lancing is described in more detail in U.S. Provisional Application No. 60/422,228, which is hereby incorporated herein by reference.

Depth penetration control with lancing device 700 is accomplished by having a threaded connection (not shown) between the plunger pull 732 and the lancet holder 714. The depth control or over-travel is limited when the plunger pull 732 contacts the lancet carriage 718. By adjusting the gap between the plunger pull 732 and the lancet carriage 718, lancet depth control is achieved. Over-travel spring 730 returns the lancet to the rest position after lancing is complete.

The floating probe 706 can be locked into a fixed position by use of dowel pins 708. Placing the floating probe into a locked position disables the floating nature of the floating probe. However, such a locked position can be desirable when lancing device 700 is used to lance a target site that results in a relatively flat (i.e., essentially flat) target site bulge. One skilled in the art will also appreciate that the slots cut into front housing 704 can be designed to allow the floating probe 706 to move in an axial direction to a prescribed limit. Except as otherwise described or illustrated, lancing device 700 operates in essentially the same manner as that described with respect to the embodiment of FIGS. 1-5.

As will be appreciated by those skilled in the art, lancet devices according to the present invention greatly facilitate reproducible production of a fluid sample (e.g., a blood sample) at a puncture (lancing) site because of the consistent lancet penetration depth. For example, lancing device 700 was employed to lance various dermal tissue target sites (i.e., an index finger target site and a palm target site) that resulted in the creation of target site bulges of various heights. Although the height of the target site bulges differed by 3 mm to 4 mm, penetration depth was consistent, and a blood sample was successfully expressed, at each target site. This facilitates in-situ testing of a fluid sample by means of a fluid collection device (such as a test strip) that is introduced at the lancet penetration site just after a lancet has been retracted. Consistent proper lancet depth control can also result in less pain.

Figure 9:
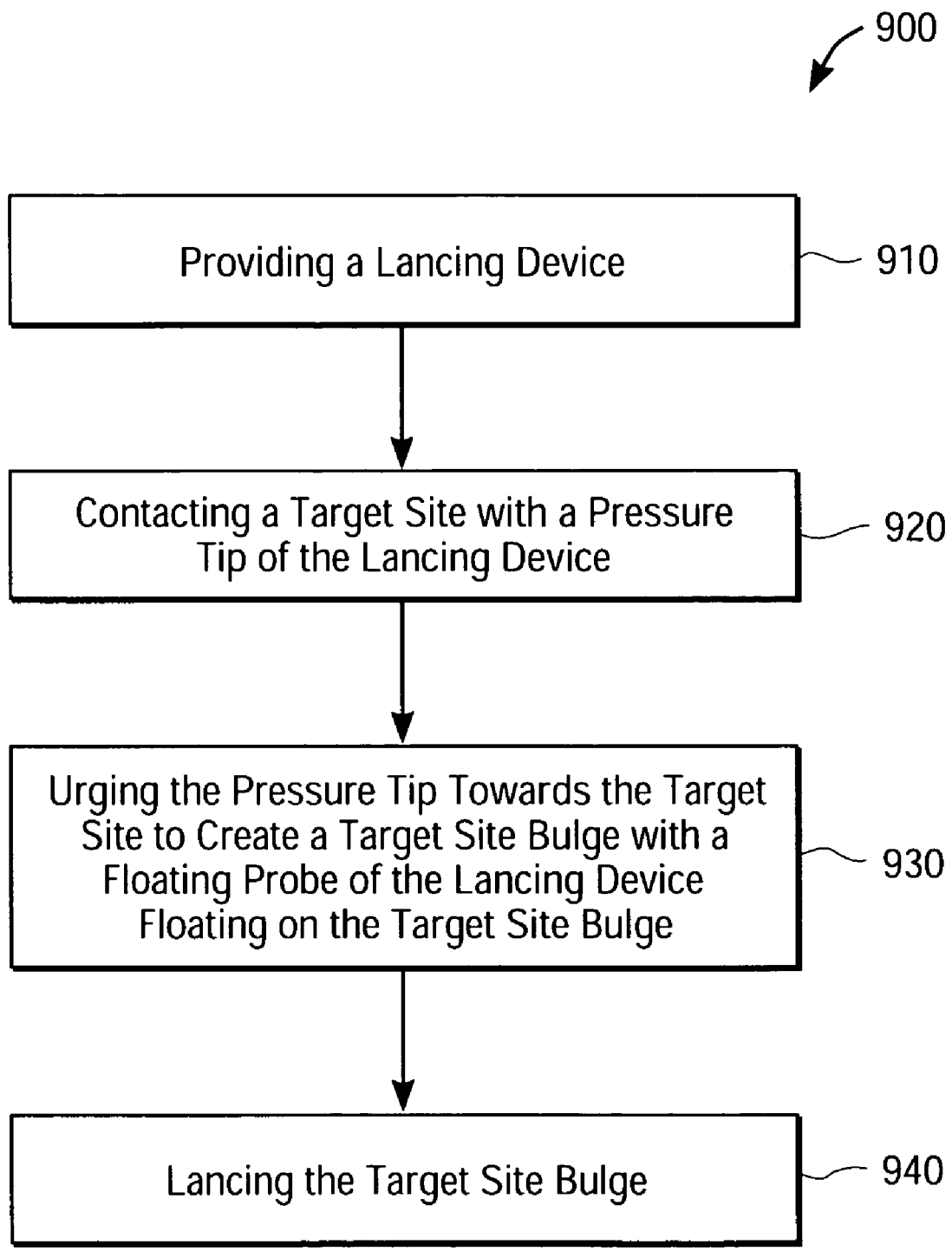
FIG. 9 is a flow diagram illustrating a sequence of steps for lancing a target site according to the present invention.

Referring to FIG. 9, a method 900 for lancing a target site includes providing a lancing device according to the present invention as described above. Such a lancing device includes a lancet carriage, a lancet holder slidably connected to the lancet carriage, a lancet attached to the lancet holder, a floating probe, and a pressure tip for engaging the target site and creating a target site bulge. The floating probe of such a lancing device is adapted to floatably contact the target site bulge and is configured to operatively interact with the lance carriage to control a penetration depth of the lancet into the target site bulge, as set forth in step 910.

Next, at step 920, the pressure tip of the lancing device is contacted with the target site. Subsequently, the pressure tip is urged towards the target site, thereby creating target site bulge with the floating probe floating (resting) on a surface of the target site bulge, as set forth in step 930.

Next, the target site bulge is lanced with the lancet while the floating probe operatively interacts with the lance carriage to control a penetration depth of the lancet into the bulge, as set forth in step 940. If desired, movement of the floating probe during lancing can be prevented through the use of a stop lock assembly as described above. One skilled in the art will recognize that steps 910, 920, 930 and 940 have been effectively illustrated by FIGS. 2 through 4B above.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A lancing device comprising:
   a lancing mechanism having:
   a lancet carnage;
   a lancet holder slidably connected to the lancet carriage;
   a lancet attached to the lancet holder; and
   a lock-stop assembly;
   a floating probe; and
   a pressure tip for engaging a target site and creating a target site bulge;
   wherein the floating probe is adapted to floatably rest upon said target site bulge as said target site bulge is created by the pressure tip and is configured to operatively interact with the lancet carriage to control a penetration depth of the lancet into the target site bulge, and further configured to engage the lock-stop assembly to prevent movement of the floating probe during penetration of the lancet into the target site bulge.

2. The lancing device of claim 1 further comprising:
   a housing;
   wherein the lancet carriage is slidably connected to the housing, the lancet holder is slidably connected to the lancet carriage and the floating probe is slidably connected to the housing.

3. The lancing device of claim 1, wherein the floating probe is formed from a rigid material.

4. The lancing device of claim 1, further comprising a launcher spring and a decoupling spring arranged in series.

5. The lancing device of claim 1, wherein the penetration depth is in the range of 0.25 to 1.5 mm.

6. The lancing device of claim 2, wherein the lancing mechanism further includes an over-travel spring and a launcher spring, wherein the housing includes a floating probe spring, and wherein the floating probe spring, and launcher spring are configured to control movement and positioning of the floating probe, lancet carriage and lancet holder.

7. The lancing device of claim 1, wherein the pressure tip includes a probe stop surface.

8. The lancing device of claim 1, wherein the lancet carriage includes a lancet holder over-travel stop feature.

9. A method for lancing a target site, the method comprising:
   providing a lancing device that includes:
      a lancet carnage;
      a lancet holder slidably connected to the lancet carriage; and
      a lancet attached to the lancet holder;
      a floating probe;
      a stop lock assembly; and
      a pressure tip for engaging a target site and creating a target site bulge;
   wherein the floating probe is adapted to floatably rest upon said target site bulge as said target site bulge is created by the pressure tip and is configured to operatively interact with the lancet carriage to control a penetration depth of the lancet into the target site bulge;
   contacting the pressure tip with the target site;
   urging the pressure tip towards the target site, thereby creating the target site bulge as the floating probe is floating on a surface of the target site bulge; and
   lancing the target site bulge with the lancet while the floating probe operatively interacts with the lancet carriage to control a penetration of the lancet while the stop lock assembly prevents movement of the floating probe.

\* \* \* \* \*